US009835592B2

(12) United States Patent
Yusuf et al.

(10) Patent No.: US 9,835,592 B2
(45) Date of Patent: Dec. 5, 2017

(54) DETERMINATION OF TUBERCULATION IN A FLUID DISTRIBUTION SYSTEM

(71) Applicant: Mueller International, LLC, Atlanta, GA (US)

(72) Inventors: Shabbir Yusuf, Mississauga (CA); Werner Guenther Richarz, Thornhill (CA)

(73) Assignee: Mueller International, LLC, Atlanta, GA (US)

( * ) Notice: Subject to any disclaimer, the term of this patent is extended or adjusted under 35 U.S.C. 154(b) by 245 days.

(21) Appl. No.: 14/740,902

(22) Filed: Jun. 16, 2015

(65) Prior Publication Data

US 2016/0370325 A1 Dec. 22, 2016

(51) Int. Cl.
| | | |
|---|---|---|
| G01N 29/04 | (2006.01) |
| G01N 29/032 | (2006.01) |
| G01N 29/07 | (2006.01) |
| G01N 29/40 | (2006.01) |
| G01N 29/44 | (2006.01) |

(52) U.S. Cl.
CPC .......... *G01N 29/032* (2013.01); *G01N 29/07* (2013.01); *G01N 29/40* (2013.01); *G01N 29/4454* (2013.01); *G01N 29/449* (2013.01); *G01N 2291/015* (2013.01); *G01N 2291/0258* (2013.01); *G01N 2291/02416* (2013.01); *G01N 2291/103* (2013.01)

(58) Field of Classification Search
CPC .. G01N 29/032; G01N 29/4454; G01N 29/07; G01N 29/40; G01N 29/449; G01N 29/12; G01N 29/043; G01N 29/4427; G01N 29/024
See application file for complete search history.

(56) References Cited

U.S. PATENT DOCUMENTS

| | | |
|---|---|---|
| 4,929,898 A | 5/1990 | Spies |
| 5,526,689 A | 6/1996 | Coulter et al. |
| 6,556,924 B1 | 4/2003 | Kariyawasam et al. |
| 6,561,032 B1 | 5/2003 | Hunaidi |

(Continued)

FOREIGN PATENT DOCUMENTS

| | | |
|---|---|---|
| FR | 2754898 | 4/1998 |
| WO | 2010020817 | 2/2010 |

(Continued)

OTHER PUBLICATIONS

Coleman, Matthew, Simon; International Search Report and Written Opinion for PCT Application No. PCT/US2016/020889, filed Mar. 4, 2016, dated Jun. 6, 2016, 14 pgs.

(Continued)

*Primary Examiner* — Helen Kwok
(74) *Attorney, Agent, or Firm* — Taylor English Duma LLP

(57) ABSTRACT

Examples of determining tuberculation in a fluid distribution system are disclosed. In one example implementation according to aspects of the present disclosure, an acoustical wave generator generates an acoustical wave within a fluid path of a fluid distribution system. A first acoustical sensor and a second acoustical sensor sense the acoustical wave. An acoustical signal analysis module determines an amount of tuberculation within the fluid distribution system by analyzing the sensed acoustical wave.

17 Claims, 6 Drawing Sheets

(56) References Cited

U.S. PATENT DOCUMENTS

| | | | |
|---|---|---|---|
| 7,266,992 B2* | 9/2007 | Shamout | G01M 3/243 73/40.5 A |
| 7,328,618 B2 | 2/2008 | Hunaidi et al. | |
| 7,475,596 B2 | 1/2009 | Hunaidi et al. | |
| 7,810,378 B2 | 10/2010 | Hunaidi et al. | |
| 7,830,273 B2* | 11/2010 | Twitchell, Jr. | H04L 67/125 340/854.5 |
| 8,296,083 B2* | 10/2012 | Martin | G01M 3/243 340/605 |
| 8,816,866 B2* | 8/2014 | Day | G01F 1/666 340/603 |
| 8,966,979 B2* | 3/2015 | Amundsen | G01B 7/066 73/40.5 A |
| 9,541,432 B2* | 1/2017 | Kertesz | H01M 2/1022 |
| 2001/0032064 A1 | 10/2001 | Araki et al. | |
| 2003/0033870 A1 | 2/2003 | Shah et al. | |
| 2003/0033879 A1* | 2/2003 | Adewumi | G01N 29/07 73/627 |
| 2005/0210960 A1 | 9/2005 | Shamout et al. | |
| 2006/0283251 A1 | 12/2006 | Hunaidi | |
| 2007/0041333 A1* | 2/2007 | Twitchell | G08B 25/009 370/252 |
| 2009/0250125 A1* | 10/2009 | Howitt | E03F 7/00 137/551 |
| 2012/0125111 A1 | 5/2012 | Groos et al. | |
| 2012/0167688 A1 | 7/2012 | Minachi et al. | |
| 2013/0211797 A1* | 8/2013 | Scolnicov | G06Q 50/06 703/2 |
| 2013/0240093 A1 | 9/2013 | Okada | |
| 2016/0208952 A1* | 7/2016 | Howitt | F16K 37/0075 |
| 2016/0223120 A1* | 8/2016 | Gagliardo | F16L 55/1645 |
| 2016/0252422 A1* | 9/2016 | Howitt | G01M 3/2807 |
| 2016/0290974 A1 | 10/2016 | Coleman et al. | |
| 2017/0176395 A1 | 6/2017 | Burtea | |
| 2017/0248555 A1 | 8/2017 | Yusuf et al. | |

FOREIGN PATENT DOCUMENTS

| | | |
|---|---|---|
| WO | 2015073313 | 5/2015 |
| WO | 2016160267 | 10/2016 |

OTHER PUBLICATIONS

De Silva et al., Condition Assessment and Probabilistic Analysis to Estimate Failure Rates in Buried Pipelines, Thermo Scientific, In: Proceedings of ASTT 5th Conference. Aug. 2002 {Aug. 2002}. Retrieved from <https://www.researchgate.net/profile/Magnus_Moglia/publication/236834972_Condition_Assessment_and_Probabilistic_Analaysis_to_Estimate_Failure_Rates_in_Buried_Pipelines/links/00b7d51945e4007c48000000/pdf>, 21 pgs.

Sheppard et al., Cast Iron Fitness for Purpose (FFP)—Final Report, Macaw Engineering, Ltd., Jun. 3, 2015, Retrieved from <http://www.smartemetworks.org/Files/Cast_Iron_Fitness_For_Purpose_{CIFFP}_151214123856.pdf>, 91 pgs.

Yusuf, Shabbir; PCT Application entitled: A Determination of Tuberculation in a Fluid Distribution System, having serial No. PCT/US2016/036856, filed Jun. 10, 2016, 27 pgs.

Yusuf, Shabbir; International Search Report and Written Opinion for serial No. PCT/US2016/036856, filed Jun. 10, 2016, dated Sep. 9, 2016, 10 pgs.

Baik, et al; Article entitled: "Acoustic attenuation, phase and group velocities in liquid-filled pipes: Theory, experiment, and examples of water and mercury", J. Acoust. Soc. Am. 128(5), Nov. 2010, 15 pgs.

Coleman, Matthew Simon; U.S. Patent Application entitled: Determination of Pipe Wall Failure Based on Minimum Pipe Wall Thickness, U.S. Appl. No. 14/674,851, filed Mar. 31, 2015, 31 pgs.

Hay, Lindsay; "The Influence of Soil Properties on the Performance of Underground Pipelines", Department of Soil Science, The Faculty of Agriculture, The University of Sydney, Aug. 1984, 243 pgs.

Makar, et al.; "Failure Modes and Mechanisms in Gray Cast Iron Pipe", National Research Council Canada, Copyright 2000, 11 pgs.

Muster, et al.; "Life Expectancy of Cement Mortar Linings in Cast and Ductile Iron Pipes", Water Research Foundation, Copyright 2011, 192 pgs.

Rajani, et al.; "Impact of Soil Properties on pipe corrosion: re-examination of traditional conventions", National Research Council Canada, Sep. 2010, 17 pgs.

Rajani, et al.; "Investigation of Grey Cast Iron Water Mains to Develop a Methodology for Estimating Service Life", AWWA Research Foundation, Copyright 2000, 294 pgs.

Sewerin; Operating Instructions for Combiphon, dated Dec. 10, 2011; 32 pgs.

Burtea, Valentin Mircea; U.S. Patent Application entitled: Noisemaker for Pipe Systems, U.S. Appl. No. 14/974,351, filed Dec. 18, 2015, 25 pgs.

Yusuf, Shabbir; U.S. Patent Application entitled: External Noisemaker for Pipe Systems U.S. Appl. No. 15/056,403, filed Feb. 29, 2016, 29 pgs.

Coleman, Matthew Simon; PCT Application entitled: Determination of Pipe Wall Failure Based on Minimum Pipe Wall Thickness U.S. Appl. No. PCT/US16/20889, filed Mar. 4, 2016, 35 pgs.

Coleman, Matthew Simon; Non-Final Office Action for U.S. Appl. No. 14/674,851, filed Mar. 31, 2015, dated Jun. 16, 2017, 50 pgs.

* cited by examiner

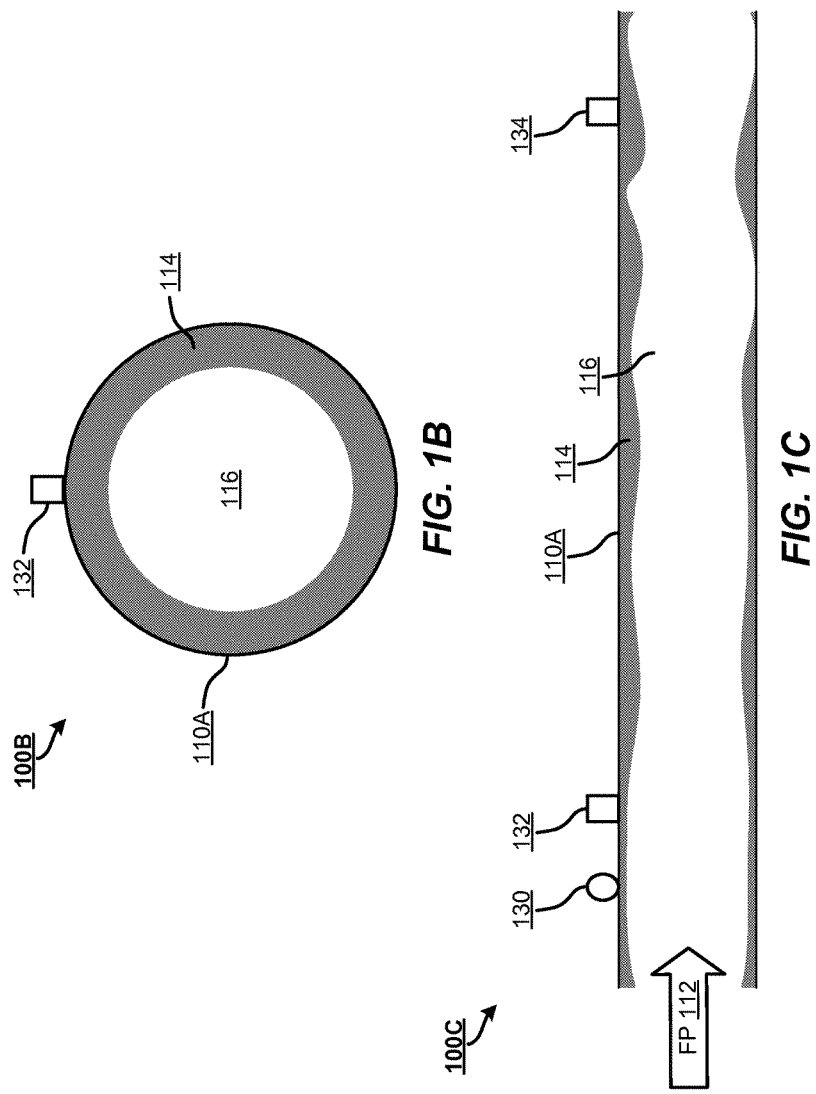

DETERMINATION OF TUBERCULATION IN A FLUID DISTRIBUTION SYSTEM

BACKGROUND

A utility provider may install and maintain infrastructure to provide utility services to its customers. For example, a water utility provider may implement a fluid distribution system to distribute water to its customers. Over time, the interior of the fluid distribution system and its components (e.g., pipes, valves, couplings, etc.) may accumulate mineral deposits, causing the fluid distribution system to become less efficient at distributing the fluid.

BRIEF DESCRIPTION OF THE DRAWINGS

The following detailed description references the drawings, in which:

FIG. 1B illustrates a cross sectional view of a pipe of the fluid distribution system of FIG. 1A taken in a plane extending in the radial direction and orthogonal to the longitudinal direction according to examples of the present disclosure;

FIG. 1C illustrates a cross sectional view of a pipe of the fluid distribution system of FIG. 1A taken in a plane extending in the radial and longitudinal directions according to examples of the present disclosure;

DETAILED DESCRIPTION

Figure 1A:
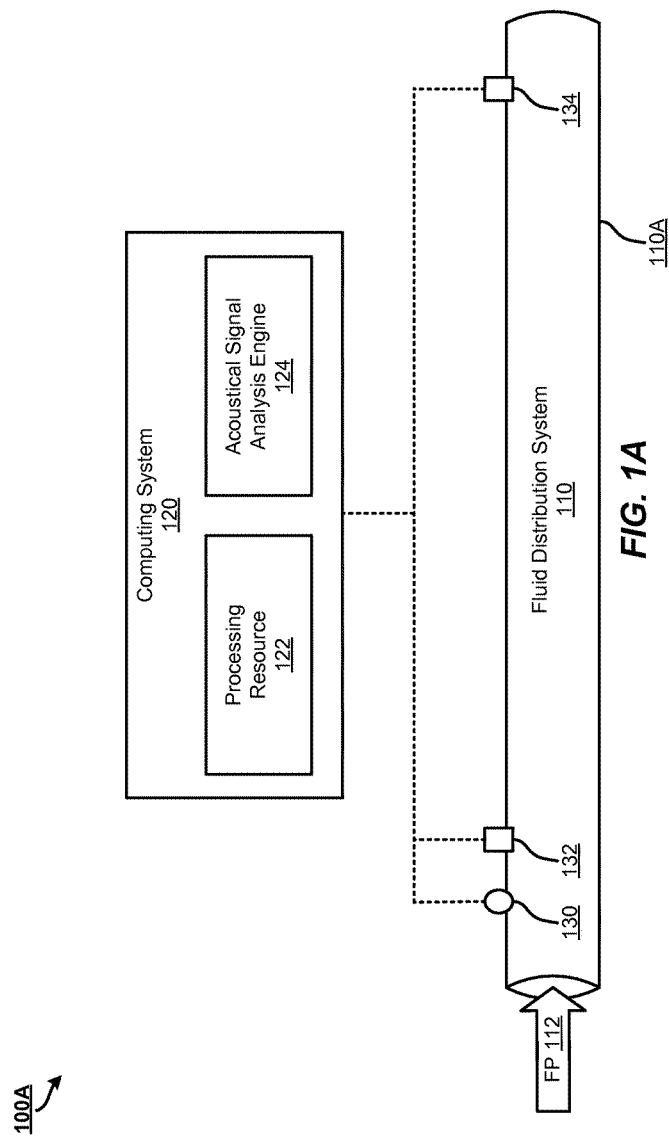
FIG. 1A illustrates a diagram of an environment to determine an amount of tuberculation within a fluid distribution system according to examples of the present disclosure.

A utility provider may utilize a fluid distribution system to distribute fluids such as water or gas to its customers. To provide the fluid to its customers effectively, the utility provider may desire to monitor the efficiency and integrity of the fluid distribution system. Over time, as the fluid flows through the fluid distribution system, mineral deposits may accumulate within the fluid distribution system. The accumulation of mineral deposits, known as tuberculation, decreases the cross-sectional area of the fluid distribution system, which is detrimental to efficient fluid distribution through the fluid distribution system. For example, a pipe within the fluid distribution system has a cross-section through which the fluid flows. As tuberculation increases (i.e., as minerals build up within the pipe or other component of the fluid distribution system), the cross-section of the pipe decreases, thereby decreasing the volume of fluid that can flow through the pipe.

It is therefore desirable to determine the amount of tuberculation within a fluid distribution system to assess the efficiency and integrity of the fluid distribution system. Additionally, from the perspective of leak detection and condition assessment of the fluid distribution system, tuberculation poses certain challenges. For example, the mineral deposits, which are a porous material, absorb acoustic energy propagating along the fluid distribution system (such as when detecting leaks or assessing the condition of the fluid distribution system). This absorption negatively influences acoustic signaling used for leak detection and/or condition assessment. By determining the amount of tuberculation within the fluid distribution system, leaks can be more accurately detected and the condition of the fluid distribution system can be more accurately determined.

Various implementations are described below by referring to several examples of determining tuberculation in a fluid distribution system. In one example implementation according to aspects of the present disclosure, an acoustical wave generator generates an acoustical wave within a fluid path of a fluid distribution system. A first acoustical sensor and a second acoustical sensor sense the acoustical wave. An acoustical signal analysis module determines an amount of tuberculation within the fluid distribution system by analyzing the sensed acoustical wave. Other examples are described in the present disclosure.

The present disclosure enables tuberculation to be determined within a fluid distribution system. For example, a fluid distribution system maintainer (e.g., a water utility provider) may utilize the present techniques to detect the presence and amount of tuberculation within the water distribution system. By detecting the tuberculation, the fluid distribution system maintainer may evaluate the remaining lifetime of the fluid distribution system and its components. The fluid distribution system maintainer may also be enabled to replace components of the fluid distribution system when tuberculation reaches a certain threshold, for example, or may take preventative measures to reduce the amount of tuberculation present in the fluid distribution system. These and other advantages will be apparent from the description that follows.

Figure 2:
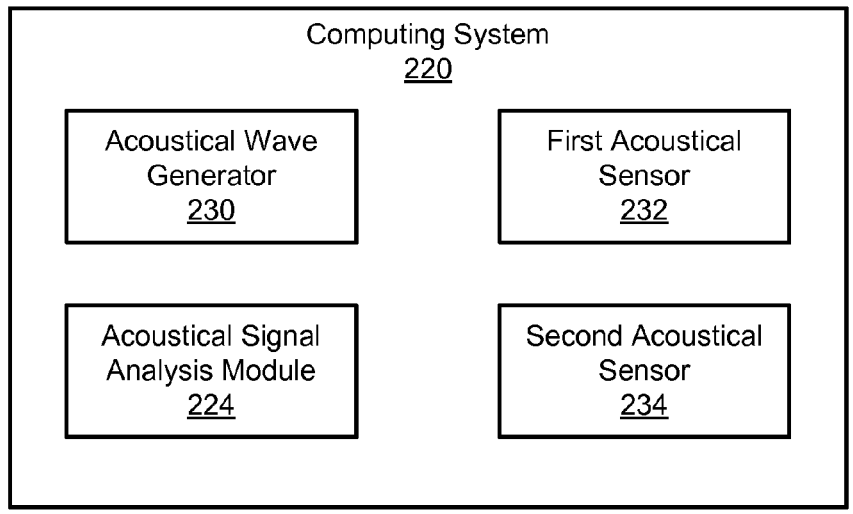
FIG. 2 illustrates a block diagram of a computing system to determine an amount of tuberculation within a fluid distribution system, such as the fluid distribution system of FIG. 1A, according to examples of the present disclosure.
Figure 3:
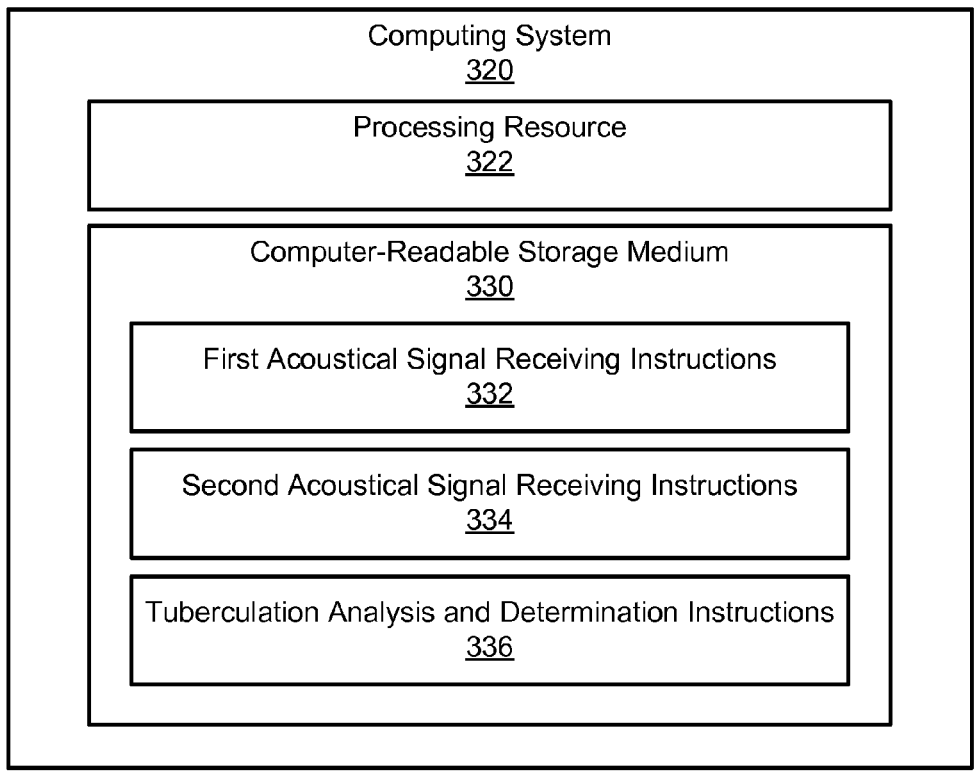
FIG. 3 illustrates a computer-readable storage medium storing instructions to determine tuberculation in a fluid distribution system according to examples of the present disclosure.

FIGS. 1-3 include particular components, modules, instructions, engines, etc. according to various examples as described herein. In different implementations, more, fewer, and/or other components, modules, instructions, engines, arrangements of components/modules/instructions/engines, etc. may be used according to the teachings described herein. In addition, various components, modules, engines, etc. described herein may be implemented as instructions stored on a computer-readable storage medium, hardware modules, special-purpose hardware (e.g., application specific hardware, application specific integrated circuits (ASICs), embedded controllers, hardwired circuitry, etc.), or some combination or combinations of these.

Generally, FIGS. 1-3 relate to components and modules of a computing system, such as computing system 120 of FIG. 1A, computing system 220 of FIG. 2, and computing system 320 of FIG. 3. It should be understood that the computing systems 120, 220, and 320 may include any appropriate type of computing system and/or computing device, including for example smartphones, tablets, desktops, laptops, workstations, servers, smart monitors, smart televisions, digital signage, scientific instruments, retail point of sale devices, video walls, imaging devices, peripherals, networking equipment, wearable computing devices, or the like.

FIG. 1A illustrates a diagram of an environment 100 to determine an amount of tuberculation within a fluid distribution system 110 according to examples of the present disclosure. In examples, an acoustical wave generator 130 generates an acoustical wave within a fluid path 112 of a fluid distribution system 110. A first acoustical sensor 132 and a second acoustical sensor 134 sense the acoustical wave. An acoustical signal analysis module 124 determines an amount of tuberculation within the fluid distribution system by analyzing the sensed acoustical wave.

As illustrated, the environment 100 includes a fluid distribution system 110, which may further include a pipe 110A. Although illustrated as the pipe 110A, it should be understood that the fluid distribution system 110 may be a plurality of pipes and other fluid distribution system components connected together to form the fluid distribution system 110, of which the pipe 110A is a portion.

Generally, fluid distribution system 110 may be used to distribute fluids such as water to customers of a utility provider, for example. The fluid distribution system 110 may include various and numerous components, such as pipes (e.g., pipe 110A), hydrants, valves, couplers, corporation stops, and the like, as well as suitable combinations thereof. In examples, the fluid distribution system 110 may be partially or wholly subterranean, or portions of the fluid distribution system 110 may be subterranean, while other portions of the fluid distribution system 110 may be non-subterranean (i.e., above ground). For example, a pipe such as pipe 110A may be partially or wholly subterranean while a hydrant or valve (not shown) connected to the pipe 110A may be partially or wholly non-subterranean. In other examples, the pipe 110A may be partially subterranean in that the pipe 110A has portions exposed, such as to connect testing devices (e.g., acoustical wave generator 130, first acoustical sensor 132, second acoustical sensor 134, etc.) to the pipe 110A.

The acoustical wave generator 130 generates an acoustical wave within the fluid path 112 within the fluid distribution system 110. In examples, the acoustical wave generator 130 is in fluid communication with fluid path 112 within the fluid distribution system 110, and the acoustical wave generator 130 generates an acoustical wave. As illustrated in FIG. 1A, the acoustical wave generator 130 is connected to the pipe 110A of the fluid distribution system 110. In examples, the connection may be direct and/or indirect. More particularly, acoustical wave generator 130 may be connected directly to the pipe 110A, such as through a hole drilled into the wall of the pipe 110A, thereby causing the acoustical wave generator 130 to be in fluid communication with the flow path 112. In some examples, the acoustical wave generator 130 may extend partially or wholly into the flow path 112, while in other examples, the acoustical wave generator 130 may not extend into the flow path 112. In another example, the acoustical wave generator 130 may be connected indirectly to the pipe 110A, such as via another component in the fluid distribution system 110 (e.g., a hydrant, a valve, a coupler, a corporation stop, etc.). In other examples, the acoustical wave generator 130 and the first and second acoustical sensors 132 and 134 may be connected to the water distribution system 110 via air relief valves or may be hydrophones placed laterally on the pipe (e.g., pipe 110A). In some examples, the acoustical wave generator 130 may include a signal generator to generate a signal, a signal amplifier to amplify the signal, and a sound source to emit the amplified signal.

In examples, the first acoustical sensor 132 and the second acoustical sensor 134 are placed a distance apart to enabling the sensing of the acoustical wave. Such a distance may be hundreds millimeters, hundreds meters, or even several kilometers apart. In some cases, the first acoustical sensor and the second acoustical sensor may be connected to the same pipe segment, such as pipe 110A, but in other examples, the first acoustical sensor 132 and the second acoustical sensor 134 may be placed on separate portions of the fluid distribution system 110.

The acoustical wave generator 130 may be a hydrophone used in reverse (a reverse hydrophone) to produce an acoustical wave. In another example, the acoustical wave generator 130 may be a speaker or similar electronic device to produce an acoustical wave. Any suitable device capable of creating an acoustical wave, such as a pressure wave, in a fluid may be implemented as acoustical wave generator 130. For example, a pressure wave may be created manually (such as by a hammer striking the pipe) or automatically (such as by a piston striking the pipe). In addition to striking the pipe directly, a component attached to the pipe, such as a hydrant, valve, etc., may also be stricken. In another example, a valve may be opened and closed one or more times so as to generate an acoustical wave within the water flowing through the pipe. It should be understood that other techniques may be implemented to cause the acoustical wave. It should also be understood that the term "acoustic" may mean sound and/or vibration.

Once the acoustical wave generator 130 generates the acoustical wave, the first acoustical sensor 132 and the second acoustical sensor 134 sense the acoustical wave caused by a change of pressure in the flow path 112. In examples, the first acoustical sensor 132 is in fluid communication with the fluid path 112 within the fluid distribution system 110, and the first acoustical sensor 132 senses the acoustical wave generated by the acoustical wave generator 130. The first acoustical sensor 132 outputs a first acoustical signal representative of the acoustical wave, which may be received at the computing system 120, for example. Similarly, in examples, the second acoustical sensor 134 is in fluid communication with the fluid path 112 within the fluid distribution system 110, and the second acoustical sensor 134 also senses the acoustical wave generated by the acoustical wave generator 130. The second acoustical sensor 134 outputs a second acoustical signal representative of the acoustical wave, which may be also received at the computing system 120, for example. In such an implementation, the computing system 120 receives both the first and second acoustical signals from the first and second acoustical sensors 132 and 134 respectively.

The first and second acoustical sensors 132 and 134 may transmit the first and second acoustical signals respectively to the computing system 120 via a wired or wireless network or other communicative path illustrated in FIG. 1A as dotted lines. In examples, such as shown in FIG. 1A, the acoustical wave generator 130 and the first and second acoustical sensors 132 and 134 may be communicatively coupleable to one another and to the computing system 120. In examples, the acoustical wave generator 130 and the first and second acoustical sensors 132 and 134 may include transceivers, which may communicate data, such as the first and second acoustical signals, between the acoustical wave generator 130, the first and second acoustical sensors 132 and 134, and the computing system 120, which may include an interface (not shown) for transmitting and receiving the data. The transceivers may be any suitable device for sending, receiving, or sending and receiving data, such as a receiver, a transmitter, a transmitter-receiver, and/or a transceiver. It should be appreciated that any suitable communication technique may be implemented to transmit the data between the acoustical wave generator 130, and the first and second acoustical sensors 132 and 134, and the computing system 120. In examples, the computing system 120 may generate a signal to cause the acoustical wave generator 130 to generate the acoustical wave. The computing system 120 may then receive the first and second acoustical signals from the first and second acoustical sensors 132 and 134 respectively.

The dotted lines of FIG. 1A illustrate communicative paths between and among the acoustical wave generator 130, the first and second acoustical sensors 132 and 134, and the computing system 120. These paths generally represent a network that may include hardware components and computers interconnected by communications channels that allow sharing of resources and information. The network may include one or more of a cable, wireless, fiber optic, or remote connection via a telecommunication link, an infrared link, a radio frequency link, or any other connectors or systems that provide electronic communication. The network may include, at least in part, an intranet, the internet, or a combination of both. The network may also include intermediate proxies, routers, switches, load balancers, and the like. The paths followed by the network between the devices as depicted in FIG. 1A represent the logical communication paths between and among these the acoustical wave generator 130, the first and second acoustical sensors 132 and 134, and the computing system 120, not necessarily the physical paths between and among the devices.

The computing system 120 may include a processing resource 122 that represents generally any suitable type or form of processing unit or units capable of processing data or interpreting and executing instructions. The processing resource 122 may be one or more central processing units (CPUs), microprocessors, and/or other hardware devices suitable for retrieval and execution of instructions. The instructions may be stored, for example, on a memory resource (not shown), such as computer-readable storage medium 330 of FIG. 3, which may include any electronic, magnetic, optical, or other physical storage device that store executable instructions. Thus, the memory resource may be, for example, random access memory (RAM), electrically-erasable programmable read-only memory (EPPROM), a storage drive, an optical disk, and any other suitable type of volatile or non-volatile memory that stores instructions to cause a programmable processor (i.e., processing resource) to perform the techniques described herein. In examples, the memory resource includes a main memory, such as a RAM in which the instructions may be stored during runtime, and a secondary memory, such as a nonvolatile memory in which a copy of the instructions is stored.

Additionally, the computing system 120 may include the acoustical signal analysis engine 124, which analyzes the first acoustical signal and the second acoustical signal to determine an amount of tuberculation within the fluid distribution system 110. In examples, the engine(s) described herein may be a combination of hardware and programming. The programming may be processor executable instructions stored on a tangible memory, and the hardware may include processing resource 122 for executing those instructions. Thus a memory resource (not shown) can be said to store program instructions that when executed by the processing resource 122 implement the engines described herein. Other engines may also be utilized to include other features and functionality described in other examples herein.

Alternatively or additionally, the computing system 120 may include dedicated hardware, such as one or more integrated circuits, Application Specific Integrated Circuits (ASICs), Application Specific Special Processors (ASSPs), Field Programmable Gate Arrays (FPGAs), or any combination of the foregoing examples of dedicated hardware, for performing the techniques described herein. In some implementations, multiple processing resources (or processing resources utilizing multiple processing cores) may be used, as appropriate, along with multiple memory resources and/or types of memory resources.

The acoustical signal analysis module 124 analyzes the first acoustical signal and the second acoustical signal to determine an amount of tuberculation within the fluid distribution system. The sound pressure difference measured by the first acoustical sensor 132 and the second acoustical sensor 134 and outputted respectively as the first acoustical signal and the second acoustical signal is proportional to the attenuation (i.e., the loss in intensity of the rate of flow of a the liquid per unit area or flux) in the flow path 112 including through the tuberculation portion 114 and the non-tuberculation portion of the fluid distribution system 110.

Figure 6:
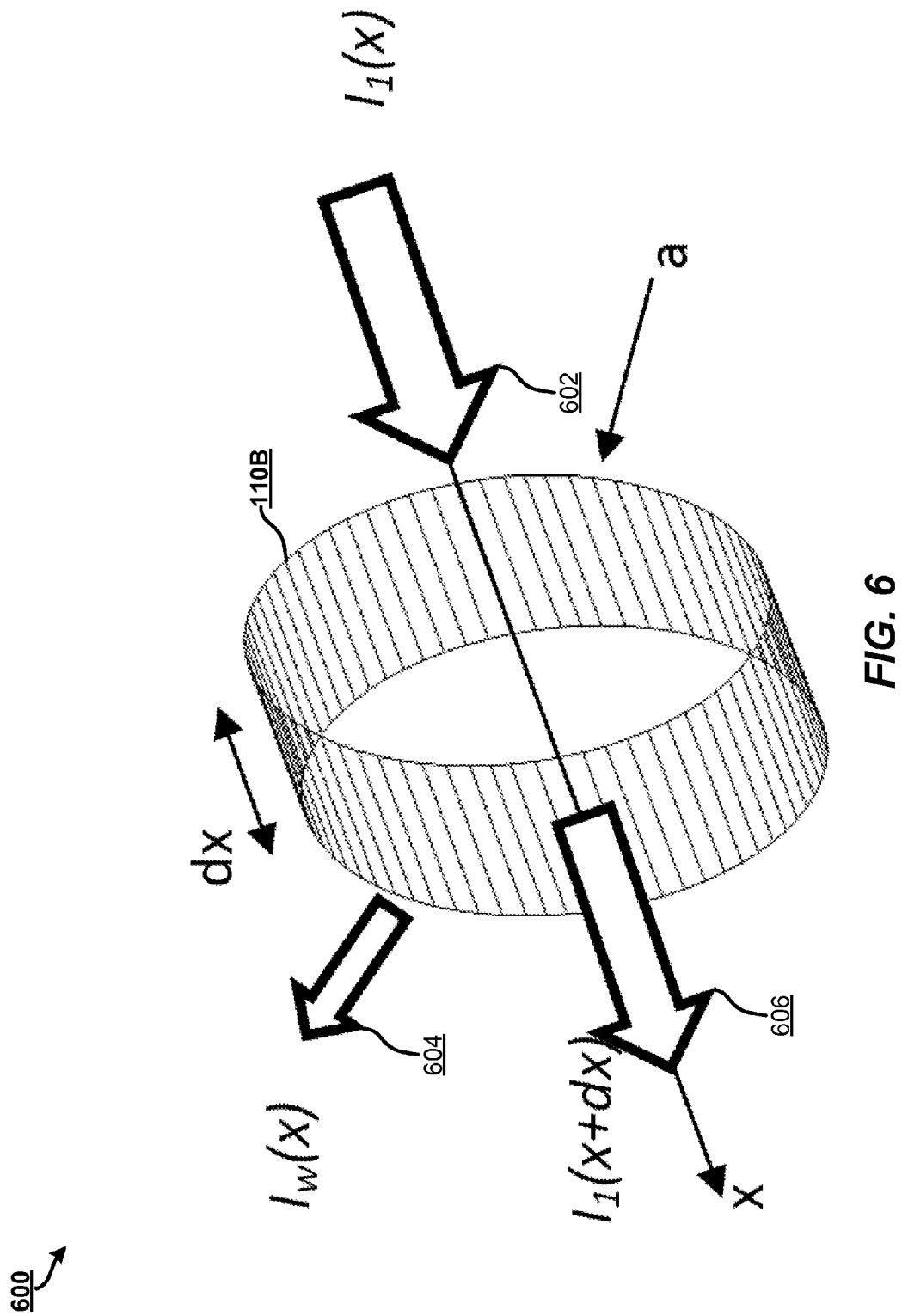
FIG. 6 illustrates a schematic of a flux of acoustic energy for a pipe segment according to examples of the present disclosure.

At frequencies below 8000 Hz, internal (molecular) attenuation within the fluid distribution system 112 are negligible, and the primary attenuation is caused by sound absorption of the fluid distribution system 110 and the tuberculation portion 114. Generally, the overall measured attenuation within the fluid distribution system 110 is a combination of the transmission loss of the acoustical wave in the flow path 112 and through the water distribution system 110 (such as through a wall of the pipe 110A) as well as the degree of tuberculation. An energy flux is illustrated in FIG. 6 below, which shows how energy passes through a section of the fluid distribution system 110. By sensing the acoustical wave and by applying standard attenuation rates for the non-tuberculation portion 116, the attenuation of the tuberculation portion 114 can be determined and thus an amount of tuberculation can also be determined. This is further described below regarding FIG. 6.

In examples, analyzing the sensed acoustical wave comprises determining a pressure difference between the sensed acoustical wave at the first acoustical sensor and the sensed acoustical wave at the second acoustical sensor. That is, energy dissipation of sound from a sound source (e.g., the acoustic wave generator 130) is determined. In additional examples, the described techniques are performed while the fluid distribution system is in use such that a fluid is flowing through the fluid distribution system 110. This may include a normal state of operation, such as when the fluid (e.g., water) is being delivered to users of the fluid distribution system 110, or during a test condition, such as leak detection.

Although not shown in FIG. 1A, it should be appreciated that the computing system 120 may include additional components. For example, the computing system 120 may include a display. The display may be or include a monitor, a touchscreen, a projection device, and/or a touch/sensory display device. The display may display text, images, and other appropriate graphical content. The computing system 120 may also include a network interface to communicatively couple the computing system 120 to the transceivers 111 and 113 via the network and to other computing systems and/or computing devices. The computing system 120 may also include any suitable input and/or output device, such as a mouse, keyboard, printer, external disk drive, or the like.

FIGS. 1B and 1C illustrate cross sectional views 100B and 100C of pipe 110A of fluid distribution system 110 of FIG. 1A. In particular, FIG. 1B illustrates a cross sectional view 100B of a pipe 110A of the fluid distribution system 110 of FIG. 1A taken in a plane extending in the radial direction and orthogonal to the longitudinal direction according to examples of the present disclosure. The pipe 110A has a tuberculation portion 114 along the inside portion of the pipe 110A between the pipe 110a and a non-tuberculation portion 116. It should be understood that, in examples, the fluid path 112 flows through the non-tuberculation portion 116 of the pipe 110A and also at least partially through the tuberculation portion 114 of the pipe 110A.

The first acoustical sensor 132 is in fluid communication with the fluid path 112 within the pipe 110A of the fluid distribution system 110. In examples, and as described herein, the first acoustical sensor 132 may be connected, directly or indirectly, to the pipe 110A or to another component or portion of the fluid distribution system 110 (e.g., hydrants, valves, couplers, corporation stops, etc.). In an example, a hole may be drilled into the pipe 110A to enable the first acoustical sensor 132 to be in fluid communication with the fluid path 112. In other examples, the first acoustical sensor 132 may be partially or wholly contained within the pipe 110A.

Although the tuberculation portion 114 is shown as being uniform in FIG. 1C, it should be appreciated that the tuberculation portion 114 may be irregular or otherwise non-uniform in examples, such as illustrated in FIG. 1C. In particular, FIG. 1C illustrates a cross sectional view 100C of a pipe 110A of the fluid distribution system 110 of FIG. 1A taken in a plane extending in the radial and longitudinal directions according to examples of the present disclosure. As in FIG. 1B, the pipe 110A has a tuberculation portion 114 along the inside portion of the pipe 110A between the pipe 110a and a non-tuberculation portion 116. In examples, the fluid path 112 flows through the non-tuberculation portion 116 of the pipe 110A and also at least partially through the tuberculation portion 114 of the pipe 110A.

The acoustical wave generator 130, the first acoustical sensor 132, and the second acoustical sensor 134 are in fluid communication with the fluid path 112 within the pipe 110A of the fluid distribution system 110. In examples, and as described herein, the acoustical wave generator 130, the first acoustical sensor 132, and the second acoustical sensor 134 may be connected, directly or indirectly, to the pipe 110A or to another component and/or components or portion of the fluid distribution system 110 (e.g., hydrants, valves, couplers, corporation stops, etc.). In an example, a hole may be drilled into the pipe 110A to enable the acoustical wave generator 130, the first acoustical sensor 132, and the second acoustical sensor 134 to be in fluid communication with the fluid path 112. In other examples, the acoustical wave generator 130, the first acoustical sensor 132, and the second acoustical sensor 134 may be partially or wholly contained within the pipe 110A.

As illustrated in FIG. 1C, the tuberculation portion 116 is non-uniform along the length of the pipe 110A. The non-uniformity may be due to corrosion by-products forming over pits in the wall of the pipe 110A, for example, or due to microbiological growth. Differences in corrosion of the wall of the pipe 110A, flow rates of the flow path 112, temperature, and other factors may all contribute to non-uniformity of the tuberculation portion 114. In other examples, as the amount of tuberculation increases in an area, some of the tuberculation may break off or otherwise separate, causing additional non-uniformity of the tuberculation portion 114.

FIG. 2 illustrates a block diagram of a computing system 220 to determine an amount of tuberculation within a fluid distribution system, such as fluid distribution system 110 of FIG. 1A, according to examples of the present disclosure. The computing system 220 may include an acoustical wave generator 230, a first acoustical sensor 232, a second acoustical sensor 234, and an acoustical signal analysis module 224. In examples, the modules described herein may be a combination of hardware and programming instructions. The programming instructions may be processor executable instructions stored on a tangible memory resource such as a computer-readable storage medium or other memory resource, and the hardware may include a processing resource for executing those instructions. Thus the memory resource can be said to store program instructions that when executed by the processing resource implement the modules described herein.

Other modules may also be utilized as will be discussed further below in other examples. In different implementations, more, fewer, and/or other components, modules, instructions, and arrangements thereof may be used according to the teachings described herein. In addition, various components, modules, etc. described herein may be implemented as computer-executable instructions, hardware modules, special-purpose hardware (e.g., application specific hardware, application specific integrated circuits (ASICs), and the like), or some combination or combinations of these.

As described above regarding acoustical wave generator 130 of FIG. 1A, acoustical wave generator 230 generates an acoustical wave within the fluid path 112 within the fluid distribution system such as fluid distribution system 110 of FIG. 1A. The first acoustical sensor 232 and the second acoustical sensor 234 then sense the acoustical wave at their respective locations and output respective first and second acoustical signals representative of the acoustical wave detected at the first and second acoustical sensors 232 and 234. In examples, the acoustical sensors may be hydrophones or other suitable devices, such as devices with piezoelectric transducers or accelerometers and the like. For example, an accelerometer may be implement to detect vibrations in the fluid distribution system. In such an example, the first acoustical sensor 232 and the second acoustical sensor 234 sensors may be on a component of the fluid distribution system, such as hydrant, valve, etc., The acoustical signal analysis module 224 then analyzes the first acoustical signal and the second acoustical signal to determine an amount of tuberculation within the fluid distribution system. For example, the acoustical signal analysis module 224 determines a pressure difference between the sensed acoustical wave at the first acoustical sensor 232 and the sensed acoustical wave at the second acoustical sensor 234. The pressure difference can be used to calculate a tuberculation portion within the fluid distribution system (e.g., tuberculation portion 114 within fluid distribution system 110 of FIG. 1A) using the techniques and principles described regarding FIG. 6.

FIG. 3 illustrates a computer-readable storage medium 330 storing instructions 332-336 to determine tuberculation in a fluid distribution system according to examples of the present disclosure. The computer-readable storage medium 330 is non-transitory in the sense that it does not encompass a transitory signal but instead is made up of one or more memory components configured to store the instructions 332-336. The computer-readable storage medium 330 may be representative of a memory resource and may store machine executable instructions 332-336, which are executable on a computing system such as computing system 120 of FIG. 1A and/or computing system 220 of FIG. 2 as well as the computing system 320 of FIG. 3 in conjunction with processing resource 322.

In the example shown in FIG. 3, the instructions 332-336 may include first acoustical signal receiving instructions 332, second acoustical signal receiving instructions 334, and tuberculation analysis and determination instructions 336. The instructions 332-336 of the computer-readable storage medium 330 may be executable so as to perform the techniques described herein, including the functionality described regarding the method 400 of FIG. 4.

Figure 4:
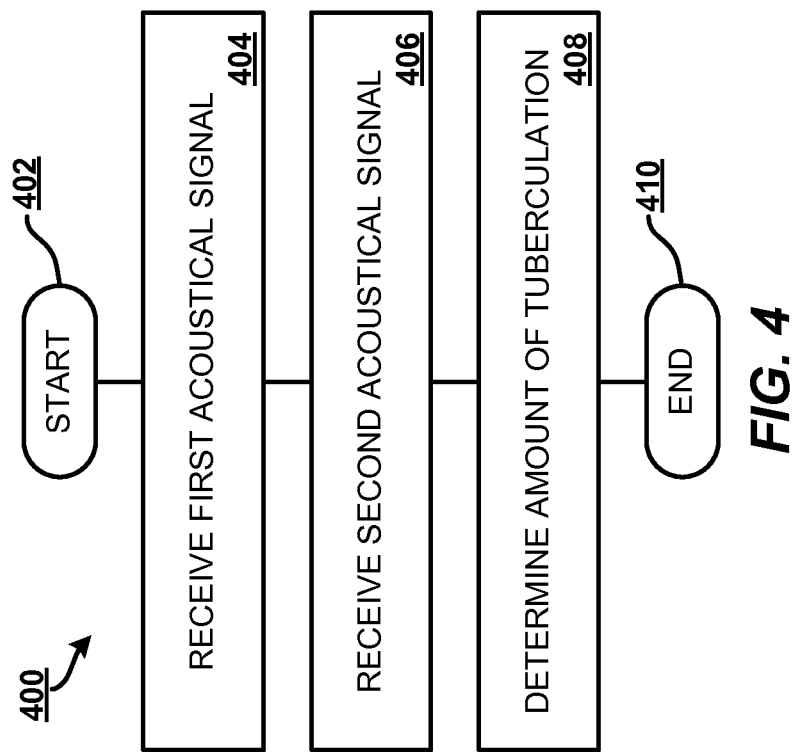
FIG. 4 illustrates a flow diagram of a method to determine tuberculation in a fluid distribution system according to examples of the present disclosure.

For example, the first acoustical signal receiving instructions 332 may correspond to block 404 of FIG. 4. The second acoustical signal receiving instructions 334 may correspond to block 406 of FIG. 4. The tuberculation analysis and determination instructions 336 may correspond to block 408 of FIG. 4. The functionality of these instructions is described below with reference to the functional blocks of FIG. 4 but should not be construed as so limiting.

In particular, FIG. 4 illustrates a flow diagram of a method 400 to determine tuberculation in a fluid distribution system according to examples of the present disclosure. The method 400 may be executed by a computing system or a computing device such as computing system 120 of FIG. 1A, computing system 220 of FIG. 2, and/or computing system 320 of FIG. 3. The method 400 may also be stored as instructions on a non-transitory computer-readable storage medium such as computer-readable storage medium 330 of FIG. 3 that, when executed by a processing resource (e.g., processing resource 122 of FIG. 1A and/or processing resource 322 of FIG. 3), cause the processing resource to perform the method 400.

At block 402, the method 400 begins and continues to block 404. At block 404, the method 400 includes receiving a first acoustical signal. For example, a computing system (e.g., computing system 120 of FIG. 1A, computing system 220 of FIG. 2, and/or computing system 320 of FIG. 3) receives a first acoustical signal output by a first acoustical sensor (e.g., first acoustical sensor 132) based on sensing an acoustical wave generated by an acoustical wave generator (e.g., acoustical wave generator 130). The method 400 continues to block 406.

At block 406, the method 400 includes receiving a second acoustical signal. For example, the computing system receives a second acoustical signal output by a second acoustical sensor (e.g., second acoustical sensor 134) based on sensing the acoustical wave generated by the acoustical wave generator (e.g., acoustical wave generator 130). The method 400 continues to block 408.

At block 408, the method 400 includes determining an amount of tuberculation. For example, the computing system determines an amount of tuberculation within a fluid distribution system by analyzing first acoustical signal and the second acoustical signal. The method 400 continues to block 410 and terminates.

Additional processes also may be included, and it should be understood that the processes depicted in FIG. 4 represent illustrations, and that other processes may be added or existing processes may be removed, modified, or rearranged without departing from the scope and spirit of the present disclosure.

Figure 5:
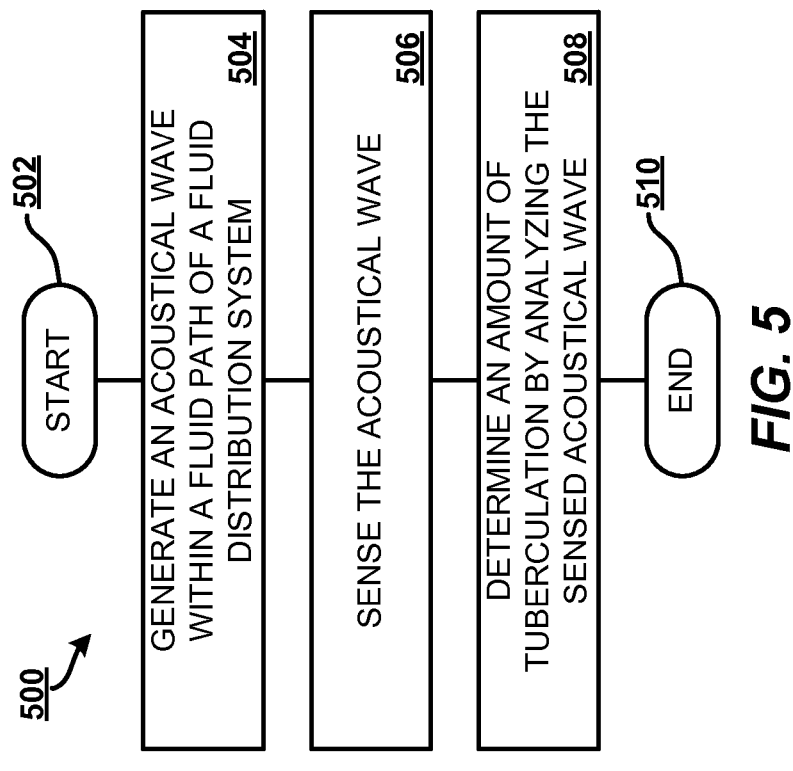
FIG. 5 illustrates a flow diagram of a method 500 to determine tuberculation in a fluid distribution system according to examples of the present disclosure.

FIG. 5 illustrates a flow diagram of a method 500 to determine tuberculation in a fluid distribution system according to examples of the present disclosure. The method 500 may be executed by a computing system or a computing device such as computing system 120 of FIG. 1A, computing system 220 of FIG. 2, and/or computing system 320 of FIG. 3. The method 500 may also be stored as instructions on a non-transitory computer-readable storage medium such as computer-readable storage medium 330 of FIG. 3 that, when executed by a processing resource (e.g., processing resource 122 of FIG. 1A and/or processing resource 322 of FIG. 3), cause the processing resource to perform the method 500.

At block 502, the method 500 begins and continues to block 504. At block 504, the method 500 includes generating an acoustical wave within a fluid path of a fluid distribution system. For example, an acoustical wave generator (e.g., acoustical wave generator 130 of FIG. 1A) generates an acoustical wave within a fluid path (e.g., flow path 112 of FIG. 1A) of a fluid distribution system (e.g., fluid distribution system 110 of FIG. 1A). The method 500 continues to block 506.

At block 506, the method 500 includes sensing the acoustical wave. For example, a first acoustical sensor (e.g., first acoustical sensor 132 of FIG. 1A) and a second acoustical sensor (e.g., second acoustical sensor 134 of FIG. 1A) sense the acoustical wave. In examples, the first acoustical sensor and the second acoustical sensor are placed a distance apart to enabling the sensing of the acoustical wave. In examples, at least one of the first acoustical sensor and the second acoustical sensor comprises a hydrophone, although other suitable sensors may be utilized. The method 500 continues to block 508.

At block 508, the method 500 includes determining an amount of tuberculation by analyzing the sensed acoustical wave. For example, an acoustical signal analysis module (e.g., acoustical signal analysis engine 124 of FIG. 1A, acoustical signal analysis module 224 of FIG. 2) determines an amount of tuberculation within the fluid distribution system (e.g., fluid distribution system 110 of FIG. 1A) by analyzing the sensed acoustical wave. In examples, analyzing the sensed acoustical wave may include determining a pressure difference between the sensed acoustical wave at the first acoustical sensor and the sensed acoustical wave at the second acoustical sensor. The method 500 continues to block 512 and terminates.

Additional processes also may be included, and it should be understood that the processes depicted in FIG. 5 represent illustrations, and that other processes may be added or existing processes may be removed, modified, or rearranged without departing from the scope and spirit of the present disclosure.

FIG. 6 illustrates a schematic 600 of a flux of acoustic energy for a pipe segment 1108 according to examples of the present disclosure. The techniques described regarding FIG. 6 may be partially and/or wholly applied by the acoustical signal analysis engine 124 of FIG. 1A, by the acoustical signal analysis module 224 of FIG. 2, and/or by the tuberculation analysis and determination instructions 336 of FIG. 3. At sufficiently low frequencies, the acoustic intensity, whose dimensions are watts/m², has a stream-wise direction "$I_1(x)$" (illustrated as arrow 602) and a radial component "$I_w(x)$" (illustrated as arrow 604) as follows:

$$\pi a^2 I_1(x) = \pi a^2 I_1 + dx) + \pi a^2 dx I_w(x) \qquad \text{Equation [1]:}$$

Equation [1] represents a statement of conversation of energy in the fluid distribution system 110 for the acoustical wave, where "a" represents the radius of the pipe. For a small "dx", $I_1(x+dx) \cong I_1(x) + dx\ dI_1(x)/dx$, so equation [1] reduces to:

$$\frac{dI_1(x)}{dx} + \frac{2}{a}I_w(x) \qquad \text{Equation [2]}$$

The loss term "$I_w(x)$" is proportional to "$I_1(x)$" as it diminishes the incident energy. In general, the proportionality factor "H (f)" is frequency dependent. Substitution into equation [2] results in the first order linear differential equation:

$$\frac{dI_1(x)}{dx} + \frac{2H(f)}{a}I_1(x) \qquad \text{Equation [3]}$$

Then, equation [3] is solvable as follows:

$$I_1(x) = I_1(0)e^{-\frac{2H(f)x}{a}} \qquad \text{Equation [4]}$$

As a result, it is shown that energy decays exponentially over distance. In the present example, "$I_1(0)$" is the initial energy at a reference (or starting) point "x=0" (such as at the acoustical wave generator 130 of FIG. 1A) The variable "x" increases in the direction of the energy propagation of the acoustical wave generated by the acoustical wave generator 130 that is away from the source (e.g., the acoustical wave generator 130). The acoustical wave diminishes over distance, as some energy is transmitted through the components of the fluid distribution system 110 (such as through a wall of pipe 110A) and radiated into the surrounding medium even without tuberculation. This contribution is "$2H_R(f)/a$." However, the presence of tuberculation (i.e., tuberculation portion 114) in the fluid distribution system 110 increases the overall attenuation of the acoustic wave generated by the acoustic wave generator 130 as follows:

$$2\frac{H_R(f) + H_T(f)}{a-t}x \qquad \text{Equation [5]}$$

Figure 7:
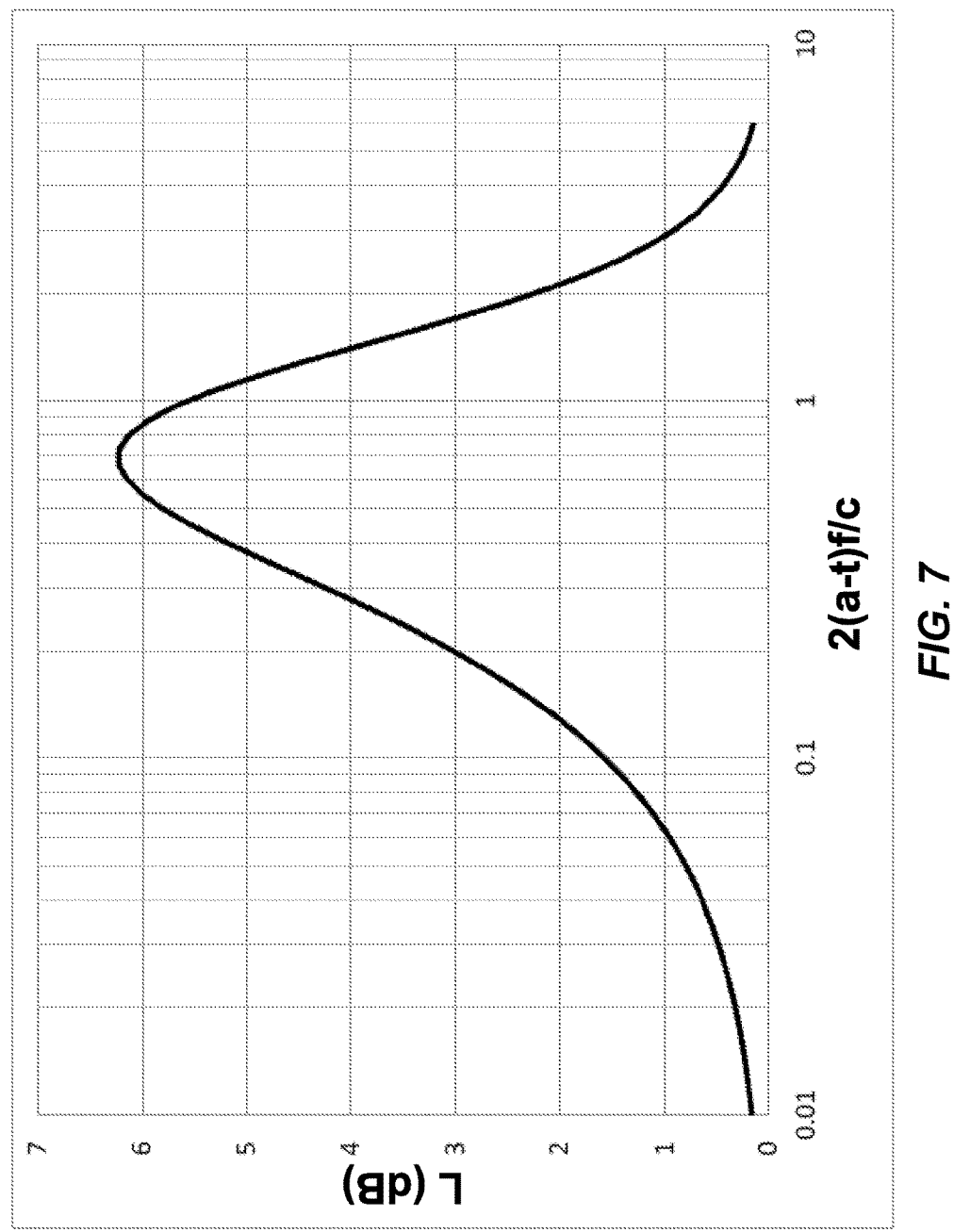
FIG. 7 illustrates a chart 700 of empirical attenuation model for tuberculation in a fluid distribution system according to examples of the present disclosure.

The reduction in the internal pipe radius "a" by the average thickness of the tuberculation region 114, denoted by the variable "t," accounts for the reduced "free area" or non-tuberculation portion 116 of the pipe 110A available for the energy flux in the "x" direction. As illustrated in FIG. 7, attenuation in may be expressed in terms of $$10\log\left(\frac{I(x)}{I(0)}\right) = \frac{Lx}{a-t} \qquad \text{Equation [6]}$$

In equation [6], "L" represents the attenuation (in dB) over a length of "a" minus "t" (radius of the pipe minus the tuberculation portion 114). As illustrated in the chart 700 of FIG. 7, the following expression is an accurate representation of the design curve if the parameters "A" and "B" are functions of "t" and "a."

$$L = \frac{A\eta}{(1+(\eta/B)^2)^2} \qquad \text{Equation [7]}$$

where "$\eta=f/f_o$" and "$f_o=0.5c/(a-t)$", c being the speed of sound in water. Also, $A=22(1-e^{-1.3t/a-t})$ and $$B = 1.25\left(\frac{t}{a-t}\right)^{-0.34}.$$

In particular, FIG. 7 illustrates a chart 700 of empirical attenuation model for tuberculation in a fluid distribution system according to examples of the present disclosure.

It should be emphasized that the above-described examples are merely possible examples of implementations and set forth for a clear understanding of the present disclosure. Many variations and modifications may be made to the above-described examples without departing substantially from the spirit and principles of the present disclosure. Further, the scope of the present disclosure is intended to cover any and all appropriate combinations and sub-combinations of all elements, features, and aspects discussed above. All such appropriate modifications and variations are intended to be included within the scope of the present disclosure, and all possible claims to individual aspects or combinations of elements or steps are intended to be supported by the present disclosure.

What is claimed is:

1. A method, comprising:
generating, by an acoustical wave generator, an acoustical wave within a fluid path of a fluid distribution system;
sensing, at a first acoustical sensor and at a second acoustical sensor, the acoustical wave;
determining, by an acoustical signal analysis module, a sound pressure difference between the acoustical wave sensed at the first acoustical sensor and the acoustical wave sensed at the second acoustical sensor, the sound pressure difference representing an attenuation of the acoustical wave within a section of the fluid distribution system between the first acoustical sensor and the second acoustical sensor; and
determining, by the acoustical signal analysis module, an amount of tuberculation within the section of the fluid distribution system based on the attenuation of the acoustical wave.

2. The method of claim 1, wherein the first acoustical sensor and the second acoustical sensor are placed a distance apart to enabling the sensing of the acoustical wave.

3. The method of claim 1, wherein at least one of the first acoustical sensor and the second acoustical sensor comprises a hydrophone.

4. The method of claim 1, wherein determining the amount of tuberculation within the section comprises relating the attenuation of the acoustical wave to the formula $$2\frac{H_R(f) + H_T(f)}{a-t}x,$$

wherein $H_R(f)$ represents a normal amount of attenuation at frequency f within the section without tuberculation, $H_T(f)$ represents an amount of attenuation at frequency f within the section contributed by tuberculation, x represents a distance along the fluid path between the first acoustical sensor and the second acoustical sensor, a represents a radius of the fluid path, and t represents an average thickness of tuberculation within the section.

5. The method of claim 1, wherein the acoustical wave generator comprises a reverse hydrophone.

6. The method of claim 1, wherein the acoustical wave generator further comprises:
a signal generator to generate a signal;
a signal amplifier to amplify the signal; and
a sound source to emit the amplified signal.

7. The method of claim 1, wherein the determining is performed while the fluid distribution system is in use such that a fluid is flowing through the fluid distribution system.

8. The method of claim 1, wherein the fluid distribution system comprises a pipe, and wherein the acoustical wave generator, the first acoustical sensor, and the second acoustical sensor are connected to the pipe.

9. A fluid distribution system, comprising:
an acoustical wave generator in fluid communication with a fluid path within the fluid distribution system, the acoustical wave generator to generate an acoustical wave;
a first acoustical sensor in fluid communication with the fluid path within the fluid distribution system, the first acoustical sensor sensing the acoustical wave generated by the acoustical wave generator and outputting a first acoustical signal representative of the acoustical wave;
a second acoustical sensor in fluid communication with the fluid path within the fluid distribution system, the second acoustical sensor sensing the acoustical wave generated by the acoustical wave generator and outputting a second acoustical signal representative of the acoustical wave; and
an acoustical signal analysis module to analyze the first acoustical signal and the second acoustical signal to determine a sound pressure difference between the acoustical wave sensed at the first acoustical sensor and the acoustical wave sensed at the second acoustical sensor, the sound pressure difference representing an attenuation of the acoustical wave within a section of the fluid distribution system between the first acoustical sensor and the second acoustical sensor, and to determine an amount of tuberculation within the section of the fluid distribution system based on the attenuation of the acoustical wave.

10. The system of claim 9, wherein the first acoustical sensor and the second acoustical sensor are placed a distance apart to enabling the sensing of the acoustical wave.

11. The system of claim 9, wherein at least one of the first acoustical sensor and the second acoustical sensor comprises a hydrophone.

12. The system of claim 9, wherein the fluid distribution system comprises a pipe.

13. The system of claim 9, wherein the acoustical wave generator comprises a reverse hydrophone.

14. The system of claim 9, wherein the acoustical wave generator further comprises:
a signal generator to generate a signal;
a signal amplifier to amplify the signal; and
a sound source to emit the amplified signal.

15. The system of claim 9, wherein the fluid distribution system comprises a pipe, and wherein the acoustical wave generator, the first acoustical sensor, and the second acoustical sensor are connected to the pipe.

16. A non-transitory computer-readable medium storing instructions that, when executed by a processing resource, cause the processing resource to:
receive a first acoustical signal output by a first acoustical sensor in a fluid distribution system based on sensing an acoustical wave generated by an acoustical wave generator;
receive a second acoustical signal output by a second acoustical sensor in the fluid distribution system based on sensing the acoustical wave generated by the acoustical wave generator;
analyze the first acoustical signal and the second acoustical signal to determine a sound pressure difference between the acoustical wave sensed at the first acoustical sensor and the acoustical wave sensed at the second acoustical sensor, the sound pressure difference representing an attenuation of the acoustical wave within a section of the fluid distribution system between the first acoustical sensor and the second acoustical sensor; and
determine an amount of tuberculation within the section of the fluid distribution system based on the attenuation of the acoustical wave.

17. The non-transitory computer-readable medium of claim 16, wherein determining the amount of tuberculation within the section comprises relating the attenuation of the acoustical wave to the formula $$2\frac{H_R(f) + H_T(f)}{a - t}x,$$

wherein $H_R(f)$ represents a normal amount of attenuation at frequency f within the section without tuberculation, $H_T(f)$ represents an amount of attenuation at frequency f within the section contributed by tuberculation, x represents a distance along a fluid path of the fluid distribution system between the first acoustical sensor and the second acoustical sensor, a represents a radius of the fluid path, and t represents an average thickness of tuberculation within the section.

* * * * *